United States Patent
Downing

(10) Patent No.: US 11,844,792 B2
(45) Date of Patent: Dec. 19, 2023

(54) TREATMENT FOR SEVERE ACUTE RESPIRATORY ILLNESS ASSOCIATED WITH CORONAVIRUS

(71) Applicant: Sean Downing, Sarasota, FL (US)

(72) Inventor: Sean Downing, Sarasota, FL (US)

( * ) Notice: Subject to any disclaimer, the term of this patent is extended or adjusted under 35 U.S.C. 154(b) by 0 days.

(21) Appl. No.: 17/372,129

(22) Filed: Jul. 9, 2021

(65) Prior Publication Data

US 2022/0008404 A1    Jan. 13, 2022

Related U.S. Application Data

(60) Provisional application No. 63/050,456, filed on Jul. 10, 2020.

(51) Int. Cl.
| | | |
|---|---|---|
| *A61K 31/47* | (2006.01) | |
| *A61P 31/14* | (2006.01) | |
| *A61K 31/192* | (2006.01) | |
| *A61K 31/165* | (2006.01) | |

(52) U.S. Cl.
CPC ............ *A61K 31/47* (2013.01); *A61K 31/165* (2013.01); *A61K 31/192* (2013.01); *A61P 31/14* (2018.01)

(58) Field of Classification Search
None
See application file for complete search history.

(56) References Cited

U.S. PATENT DOCUMENTS

| | | | | |
|---|---|---|---|---|
| 7,563,790 B2 * | 7/2009 | Eggenweiler | ............. | A61P 9/10 514/249 |
| 8,007,830 B2 * | 8/2011 | Down | ............. | A61P 11/06 424/490 |
| 9,044,479 B2 * | 6/2015 | May | ............. | A61K 31/47 |
| 2012/0132203 A1 | 5/2012 | Hodson et al. | | |
| 2013/0085124 A1 | 4/2013 | May | | |
| 2017/0266199 A1 * | 9/2017 | Berger | ............. | A61K 31/55 |
| 2019/0247304 A1 | 8/2019 | Yadidi | | |

OTHER PUBLICATIONS

Downing et al., "Colchicine, aspirin, and montelukast—A case of successful combined pharmacotherapy for adult multisystem inflammatory syndrome in COVID-19", Oct.-Dec. 2020, J. Global Infect. Dis., 12(4), pp. 221-224. (DOI: 10.4103/jgid.jgid_296_20) (Year: 2020).*

Bhattacharya et al., "Reposition of montelukast either alone or in combination with levocetirizine against SARS-CoV-2," Medical Hypothesis, Jun. 28, 2020, 144:110046, 2 pages.

Downing et al., "Colchicine, Aspirin, and Montelukast—A Case of Successful Combined Pharmacotherapy for Adult Multisystem Inflammatory Syndrome in COVID-19," J. Glob. Inf. Dis., Nov. 30, 2020, 12(4):221-224.

Gysi et al., "Network Medicine Framework for Identifying Drug Repurposing Opportunities for COVID-19," arXiv:2004.07229v1 [qbio.MN], Apr. 15, 2020, 19 pages.

Wikepedia, "C-reactive protein," Jan. 27, 2020, 14 pages.

Horby et al., "Effect of Dexamethasone in Hospitalized Patients with COVID-19—Preliminary Report," Recovery Collaborative Group, https://doi.org/10.1101/2020.06.22.20137273, Jun. 2020, 24 pages.

Ye et al., "The pathogenesis and treatment of the 'Cytokine Storm' in COVID-19," Journal of Infection, 2020, 80:607-613.

* cited by examiner

*Primary Examiner* — My-Chau T. Tran
(74) *Attorney, Agent, or Firm* — Foley & Lardner LLP

(57) ABSTRACT

A method is provided for identifying a patient having a respiratory illness and administering to the patient a combination of an anti-inflammatory agent and a leukotriene inhibitor. The method may include treating respiratory illness associated with a coronavirus, and may it may further include reducing or preventing an inflammatory response or cytokine storm for those patients without impairing their immune response against the underlying pathogen.

6 Claims, No Drawings

TREATMENT FOR SEVERE ACUTE RESPIRATORY ILLNESS ASSOCIATED WITH CORONAVIRUS

CROSS-REFERENCE TO RELATED APPLICATIONS

This application claims priority to U.S. Provisional Application No. 63/050,456, filed Jul. 10, 2020, the entire contents of which are incorporated herein by reference.

BACKGROUND OF INVENTION

Cytokine storm is a general term applied to maladaptive cytokine release in response to infection and other stimuli. The pathogenesis includes loss of regulatory control of pro-inflammatory cytokine production, both at local and systemic levels. Some evidence shows that, during coronavirus infections (COVID-19), deterioration in some patients has been associated with dysregulated and excessive cytokine release. Ye et al., *J. Infect.*, 2020 June, 80(6): 607-613.

A study called COLCORONA (clinical trial identifier: NCT04322682) is investigating the prevention of Severe Acute Respiratory Syndrome ("SARS") associated with coronavirus infections in an outpatient population. The patients test COVID positive and are discharged home to receive colchicine or placebo. Patients will receive study medication colchicine 0.5 mg per os (PO) twice daily for the first 3 days and then once daily for the last 27 days.

An inpatient study recently published called the Recovery Trial completed at Oxford University (Horby H., et. al., Recovery Collaborative Group, Effect of Dexamethasone in Hospitalized Patients with COVID-19-Preliminary Report, June 2020.) demonstrated the utility of treating SARS with steroids in COVID-19 patients. The study revealed that dexamethasone reduced mortality in ventilated patients by 33% and reduced mortality by 20% in patients receiving oxygen without mechanical ventilation. In patients not receiving respiratory support, dexamethasone had no effect.

DETAILED DESCRIPTION OF THE INVENTION

An embodiment of the present invention is a method comprising identifying a patient having a respiratory illness and administering to said patient a combination of an anti-inflammatory agent and a leukotriene inhibitor. One embodiment further relates to reducing or preventing an inflammatory response in a patient suffering from a respiratory illness associated with coronavirus infection. Reducing or preventing an inflammatory response or cytokine storm in such patients according to an aspect of this embodiment can lead to an improved outcome without impairing their immune response against the underlying pathogen.

An "anti-inflammatory agent" as used herein is an agent that reduces inflammation. In some embodiments, an anti-inflammatory agent is colchicine. In some embodiments, the anti-inflammatory agent is not a steroid.

"Aspirin" as used herein has the same meaning as is well known in the art. Aspirin irreversibly non-selectively inhibits the platelet cyclooxygenase-1 and cyclooxygenase-2. This results in the inhibition of the production of thromboxane A2 from arachidonic acid, which prevents platelet activation. Platelet aggregation in the formation of microthromboses within the microvasculature in some embodiments plays a role in SARS-CoV-2 pathology.

"Colchicine" as used herein has the same meaning as is well known in the art. Colchicine interferes with microtubule and spindle formation within the neutrophils and mast cells. Colchicine also in some embodiments decreases neutrophil transport and decreases the secretion of chemotactic factors. Colchicine in some embodiments prevents activation of the inflammasome and subsequent formation of IL-1 and IL-18. Colchicine has anti-inflammatory effects relating to disruption of microtubules and downstream cellular functions of leucocytes. At low concentrations, colchicine inhibits expression of E-selectin on endothelial cells and prevents neutrophil adhesion.

"C-reactive protein" or "CRP" as used herein has the same meaning as is well known in the art. CRP levels have been used in the early diagnosis of pulmonary disease. Elevated CRP levels have been correlated to the severity of pulmonary disease, for example, in pneumonia patients, including COVID-19 patients.

A "leukotriene inhibitor" as used herein is an agent that reduces the biological activity of leukotriene, including agents that reduce the synthesis of leukotriene and agents that antagonize a leukotriene receptor. In some embodiments, a leukotriene inhibitor comprises one or more agents selected from the group consisting of zafirlukast, montelukast, and zileuton. In some embodiments, a leukotriene inhibitor agent is montelukast.

"Montelukast" as used herein has the same meaning as is well known in the art. Montelukast is a selective antagonist of the cysteinyl leukotriene CysLT receptor which is located on lung epithelium. The cysteinyl leukotrienes (LTC, LTD, LTE) are involved in triggering airway edema, smooth muscle airway contraction and inflammation in lung tissue causing the symptoms of asthma.

"NSAID" or non-steroidal anti-inflammatory drug as used herein has the same meaning as is well known in the art. In some embodiments, an NSAID comprises one or more agents selected from the group consisting of ibuprofen, aspirin, naproxen, oxaprozin, etodolac, indomethacin, nabumetone, and diclofenac. In some embodiments, an NSAID is aspirin.

"Respiratory illness" as used herein means a condition, disease or disorder having to do with or impacting breathing in a patient. In some embodiments, a respiratory illness may be an early respiratory illness, mild to moderate respiratory illness or severe respiratory illness. In certain embodiments, a patient with early respiratory illness is characterized by exhibiting two or more of the following features: fever, chills, rigors, myalgia, headache, diarrhea, sore throat, rhinorrhea, and cough. In some embodiments, a patient with mild to moderate respiratory illness is characterized by exhibiting a fever (≥100.4° F. [38° C.]) plus one or more symptoms of lower respiratory tract illness: cough, dyspnea, and difficulty breathing. In some embodiments, a patient with severe respiratory illness is characterized by meeting the criteria for mild to moderate respiratory illness plus radiologic evidence of lung infiltrates consistent with pneumonia or acute respiratory distress syndrome (ARDS). In some embodiments, the respiratory illness is acute lung injury (ALI).

"SARS" as used herein means severe acute respiratory syndrome.

"Severe respiratory illness associated with coronavirus" or "coronavirus-related severe respiratory illness" as used herein refers to an acute or serious respiratory illness associated with an infection caused by a coronavirus pathogen. In certain embodiments, a severe respiratory illness associated with coronavirus includes, but is not limited to, SARS, Middle East respiratory syndrome (MERS), or coronavirus disease (COVID-19). The coronavirus pathogens that may cause a severe respiratory illness includes, SARS-CoV, MERS-CoV, and SARS-CoV-2.

Patients to be treated according to the present invention have or are suspected of developing a respiratory illness; have developed or are suspected to be developing a severe respiratory illness associated with coronavirus; have or are suspected of having a coronavirus-related illness; or are at risk of developing a respiratory illness or severe respiratory illness associated with coronavirus. Identification of such patients are based on their clinical presentations including evaluation of symptoms presented, blood work, diagnostic testing, potential exposure to infected individuals, travel history, and the like. In addition, patients exhibiting elevated levels of C-reactive protein (CRP), which may be a further indicator of lung disease severity in coronavirus-infected patients, may further be identified.

The patients to be treated, according to the present invention, are administered a combination of an anti-inflammatory agent and a leukotriene inhibitor. In a preferred method, the anti-inflammatory agent is colchicine and the leukotriene inhibitor is montelukast. In another embodiment, aspirin is also administered in combination with the colchicine and leukotriene inhibitor.

The methods of the present invention have been found to treat, ameliorate, prevent, or delay the onset of symptoms of a respiratory illnesses associated with coronavirus. For example, a person suspected of having COVID-19 and at risk of developing a respiratory illness may be administered a combination of colchicine and leukotriene inhibitor. In such patient, the desired response can include (1) treating or reducing the severity, duration, or intensity of respiratory illness symptoms; (2) preventing or delaying the onset of symptoms of a respiratory illness; and (3) preventing, delaying, or reducing the severity duration, or intensity of complications relating to respiratory illness.

In another embodiment, a person at risk of developing a severe acute respiratory illness associated with coronavirus may be administered the combination of the present invention. In such a patient, the desired response can include (1) treating or reducing the severity, duration, or intensity of severe acute respiratory illness symptoms; (2) preventing or delaying the onset of symptoms of a severe acute respiratory illness; and (3) preventing, delaying, or reducing the severity duration, or intensity of complications relating to severe acute respiratory illness.

Another embodiment includes identifying a person at risk of developing SARS and administering to such patient a combination of an anti-inflammatory agent and a leukotriene inhibitor. In such a patient, the desired response can include (1) treating or reducing the severity, duration, or intensity of SARS; (2) preventing or delaying the onset of symptoms of SARS; and (3) preventing, delaying, or reducing the severity duration, or intensity of complications relating to SARS.

The combination of an anti-inflammatory agent, a leukotriene inhibitor, and optionally, an NSAID, is administered in an effective amount suitable to elicit the desired biological response. When treating a patient having or suspected of developing a respiratory illness, the effective amount of the combined ingredients is that amount necessary to treat or reduce the severity, duration, or intensity of the respiratory illness and symptoms associated therewith; the amount necessary to prevent or delay the onset of respiratory illness; or prevent, delay, or reduce the severity, duration, or intensity of complications associated from the respiratory illness. For patients having or suspected of developing a severe acute respiratory illness associated with coronavirus, the effective amount of the combined ingredients is that amount necessary to treat or reduce the severity, duration, or intensity of the severe acute respiratory illness and symptoms associated therewith; the amount necessary to prevent or delay the onset of severe acute respiratory illness; or prevent, delay, or reduce the severity, duration, or intensity of complications associated from the severe acute respiratory illness. When treating a patient having or suspected of developing SARS, the effective amount is that amount necessary to treat or reduce the severity, duration, or intensity of SARS and symptoms associated therewith; the amount necessary to prevent or delay the onset of SARS; or prevent, delay, or reduce the severity, duration, or intensity of complications associated from SARS.

In another aspect of the invention, the combination of the present invention may be delivered in an amount effective to reduce the cytokine storm attributed to an infected patient's overreactive immune response to the coronavirus pathogen. In this manner, the effective amount would be that amount necessary to reduce the overreaction of cytokine production in the infected patient by reducing the amount of cytokines or the rate of cytokine production by the infected patient.

By way of example only, suitable dosage amounts for colchicine, montelukast, and aspirin in the claimed combinations are described herein.

In one embodiment, colchicine is administered in a total amount of about 0.2 mg to about 3 mg per day. In another embodiment, colchicine is administered in an amount of about 1 mg to about 2.5 mg per day. In certain preferred embodiments, colchicine is administered in an amount of about 1 mg per day, about 1.2 mg per day, about 1.4 mg per day, about 1.6, mg per day, about 1.8 mg per day, about 2.0 mg per day, about 2.2 mg per day, about 2.4 mg per day, about 2.6 mg per day, about 2.8 mg per day, or about 3.0 mg per day. The colchicine may be delivered in a single dose or multiple doses through the day to achieve the total dose amount. The total dosage of between 0.2 mg to 3 mg per day may be achieved by administering two or more daily doses until the total daily dose amount is attained, as is well known. Thus, in the case of delivering 2.4 mg per day, 1.2 mg may be delivered twice in a single day to arrive at the total daily dosage of 2.4 mg per day.

In an embodiment, montelukast is administered in a total amount of between about 1 mg to about 50 mg per day. In another embodiment, montelekast is administered in an amount of about 4 mg to about 12 mg per day. In certain preferred embodiments, montelukast is administered in an amount of about 4 mg per day, about 5 mg per day, about 6 mg per day, about 7 mg per day, about 8 mg per day, about 9 mg per day, about 10 mg per day, about 11 mg per day, or about 12 mg per day. The montelukast may be delivered in a single dose or multiple doses throughout the day to achieve the total dose amount. For example, the total dosage of between about 1 mg to about 50 mg per day may be achieved by administering two or more doses until the total daily dose amount is attained, as is well. Thus, in the case of delivering about 4 mg per day, about 2.0 mg may be delivered twice in a single day to arrive at the total daily dosage of about 4.0 mg per day.

In another embodiment of the invention, aspirin is administered in a total amount of between about 600 mg to about 4200 mg per day. In another embodiment, aspirin is administered in an amount of about 2000 mg to about 2800 mg mg per day. In certain embodiments, aspirin is administered in an amount of about 2000 mg per day, about 2200 mg per day, about 2400 mg per day, or about 2600 mg per day. The aspirin may be delivered in a single dose or multiple doses throughout the day to achieve the total dose amount. For example, the total dosage of between about 600 mg to 4200 mg per day may be achieved by administering two or more doses until the total daily dose amount is attained, as is well known. Thus, in the case of delivering about 2000 mg per day, about 1000 mg may be delivered twice in a single day to arrive at the total daily dosage of about 2000 mg per day.

The combination of colchicine, montelukast, and optionally, aspirin, may be administered to a patient in need thereof either in combination, concurrently or subsequent to each other. The administration of these components may be delivered via various routes including orally, parenterally, intravenously, intramuscularly, transdermally, buccally, subcutaneously, or other suitable routes. In one embodiment, these components are administered orally and concurrently.

In another aspect of the invention, pharmaceutical compositions are presented herein, which comprise a combination of an anti-inflammatory agent and leukotriene inhibitor and, optionally, an NSAID. In one embodiment, the pharmaceutical composition comprises the anti-inflammatory agent, colchicine. In another embodiment, the leukotriene inhibitor is zafirlukast, montelukast, and zileuton. In one embodiment, the leukotriene inhibitor is montelukast. If an NSAID is present, in an embodiment, the NSAID is aspirin. In another embodiment of the invention, the pharmaceutical composition comprises colchicine, montelukast, and optionally, an NSAID. In yet another embodiment, the pharmaceutical composition comprises colchicine, montelukast, and aspirin.

The pharmaceutical composition of the present invention can be administered by any route including orally, parenterally, intravenously, intramuscularly, transdermally, buccally, subcutaneously, or other suitable route. In one embodiment of the invention, the pharmaceutical composition of the present invention is administered orally, such as in a tablet, capsule, liquid, or other orally suitable form.

The pharmaceutical compositions of the present invention may contain colchicine in an amount of between about 0.1 mg to about 2 mg or about 0.25 mg to about 1.5 mg. In another embodiment, if colchicine is present in the pharmaceutical composition of the present invention, it is present in an amount of about 0.3 mg, about 0.4 mg, about 0.5 mg, about 0.6 mg, about 0.7 mg, about 0.8 mg, about 0.9 mg, about 1.0 mg, about 1.1 mg, about 1.2 mg, about 1.3 mg, about 1.4 mg, or about 1.5 mg.

The pharmaceutical compositions of the present invention may contain montelukast. If montelukast is present in the composition, it is present in an amount of between about 1 mg to about 10 mg or about 3 mg to about 8 mg. In another embodiment, if montelukast is present in the pharmaceutical composition of the present invention, it is present in an amount of about 1 mg, about 2 mg, about 3 mg, about 4 mg, about 5 mg, about 6 mg, about 7 mg, about 8 mg, about 9 mg, or about 10 mg.

The pharmaceutical compositions of the present invention may contain aspirin. If aspiring is present in the composition, it is present in an amount of between about 500 mg to about 2500 mg or about 1000 mg to about 1500 mg. In another embodiment, if aspirin is present in the pharmaceutical composition of the present invention, it is present in an amount of about 800 mg, about 1000 mg, about 1200 mg, about 1400 mg, about 1600 mg, about 1800 mg, about 2000 mg, about 2400 mg, about 2600 mg, or about 2800 mg.

Compositions of the present invention may further comprise other pharmaceutically acceptable ingredients, such as carriers or diluents.

The present invention can be illustrated in more detail by the following examples, however, it should be understood that the present invention is not limited thereto.

As will be apparent to those of skill in the art upon reading this disclosure, each of the individual embodiments described and illustrated herein has discrete components and features which may be readily separated from or combined with the features of any of the other several embodiments without departing from the scope or spirit of the present technology. Any recited method can be carried out in the order of events recited or in any other order, which is logically possible.

EXAMPLES

EXAMPLE 1: A 51 year old man in overall excellent health presented with a fever, shortness of breath and a cough. Two days before, he had experienced extreme fatigue. The following night he awoke with fever and headache. The next morning he described having a fever was as high as 104 F, scalp tenderness, headache, slept most of the day and moderate shortness of breath with any exertion. Cough was non-productive and elicited with deep inspiration.

Given his advancing symptoms and likelihood of having Covid-19 the patient was empirically started on a regimen to prevent Severe Acute Respiratory Syndrome (SARS).

The patient's treatment was started empirically on 650 mg of aspirin every 4 hours, colchicine 0.6 mg every 12 hours and montelukast 10 mg daily. The following day after starting treatment his fever was gone and only had an occasional headache. He still had slight fatigue. He was tested at a local hospital for SARS-CoV-2 and had some routine blood tests including a CBC with diff, HS-CRP, LDH and D-DIMER. His labs were unremarkable. The following day he lost his sense of smell, headaches resolved and fatigue was less. By 2 days later he began asking when he could start working out and if he could stop taking the medications. By this time, SARS-CoV-2 test came back positive.

EXAMPLE 2. A woman had to call EMS for her husband who was in respiratory distress. Upon arrival to the ER he was intubated and proven later to be SARS-CoV-2 positive. The woman began to experience the following symptoms: non-productive cough, fever, fatigue, anosmia and ageusia. She was treated with doxycycline twice daily, hydroxychloroquine 200 mg daily, montelukast 10 mg daily and aspirin 650 mg twice daily. The fever abated the following day. She regained her sense of smell one week later. All medications were stopped 2 weeks later. About 3 weeks from her initial symptoms, her SARS-CoV-2 nasal swab was negative for virus but she was SARS-CoV-2 antibody positive. Two months later she was back to her baseline.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

The invention claimed is:

1. A method comprising: identifying a patient having a respiratory illness caused by a SARS-CoV-2 infection, and administering to said patient a combination of an anti-inflammatory agent and a leukotriene inhibitor.

2. The method of claim 1, wherein the combination of an anti-inflammatory agent and a leukotriene inhibitor is a combination of colchicine and montelukast.

3. The method of claim 2, wherein said colchicine is administered in a total daily dose that is between 0.2 mg to 3 mg per day.

4. The method of claim 2, wherein said montelukast is administered in a total daily dose that is between 1 mg to 50 mg per day.

5. The method of claim 1, wherein the anti-inflammatory agent and the leukotriene inhibitor of the combination are administered concurrently.

6. The method of claim 5, wherein the combination of the anti-inflammatory agent and the leukotriene inhibitor is a combination of colchicine and montelukast.

\* \* \* \* \*